US011571597B1

(12) United States Patent
Barefoot (10) Patent No.: US 11,571,597 B1
(45) Date of Patent: *Feb. 7, 2023

(54) SYSTEM AND METHOD FOR PACKAGING AN ABSORBENT FOR SOLIDIFICATION OF LIQUID MEDICAL WASTE

(71) Applicant: Stewart Superabsorbents, LLC, Hickory, NC (US)

(72) Inventor: Quint Barefoot, McLeansville, NC (US)

(73) Assignee: STEWART SUPERABSORBENTS, LLC, Hickory, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/479,587

(22) Filed: Sep. 20, 2021

Related U.S. Application Data

(63) Continuation of application No. 16/122,046, filed on Sep. 5, 2018, now Pat. No. 11,123,589, which is a continuation of application No. 13/966,685, filed on Aug. 14, 2013, now abandoned.

(60) Provisional application No. 61/682,960, filed on Aug. 14, 2012.

(51) Int. Cl.
*A62D 3/00* (2006.01)
*A62D 3/30* (2007.01)

(52) U.S. Cl.
CPC ...................... *A62D 3/30* (2013.01)

(58) Field of Classification Search
CPC ....... A62D 3/30; A61M 1/0001; B65D 21/00; B65D 21/02; B65D 21/0209; B65D 21/0233
See application file for complete search history.

(56) References Cited

U.S. PATENT DOCUMENTS

| 2,667,422 | A | 1/1954 | Kauffman |
| 2,671,602 | A | 3/1954 | Vogt |
| 3,526,316 | A | 9/1970 | Kalogris |
| 4,096,947 | A | 6/1978 | Morse |
| 4,419,236 | A | 12/1983 | Hsu |
| 4,842,138 | A | 6/1989 | Sandel |
| 5,092,858 | A | 3/1992 | Benson |

(Continued)

FOREIGN PATENT DOCUMENTS

EP 1619136 7/2009

OTHER PUBLICATIONS

Medi Gel Superabsorbent Polymers printed Apr. 2, 2018.

(Continued)

*Primary Examiner* — Janine M Kreck
(74) *Attorney, Agent, or Firm* — Fish & Richardson P.C.

(57) ABSTRACT

The invention includes a system and method for delivery and storage of an absorbent for solidification of liquid waste. The system includes a plurality of nestable containers configured to receive aqueous liquid to be solidified and forming a packet safe space when nested one within another. The system also includes a plurality of packets at least partially soluble in the aqueous liquid to be solidified. The containers include at least one packet and each packet contains a solidifier for use as an absorbent composition for the aqueous liquid to be solidified. A packet may be housed within the containers inside a packet safe space. The invention also includes an improved system and method for packaging a solidifier for solidification of liquid medical wastes.

20 Claims, 7 Drawing Sheets

(56) References Cited

U.S. PATENT DOCUMENTS

| | | | |
|---|---|---|---|
| 5,284,621 A | 2/1994 | Kaufman | |
| 5,391,351 A | 2/1995 | Kaugman | |
| 6,797,857 B2 | 9/2004 | Tanhehco | |
| 7,291,674 B2 | 11/2007 | Kang et al. | |
| 8,450,389 B1 | 5/2013 | Barefoot | |
| 11,123,589 B1 * | 9/2021 | Barefoot | C02F 1/687 |

OTHER PUBLICATIONS

China Sumitomo SA60n Super Absorbent Polymer (SAP) printed Apr. 2, 2018.
Norsocryl® S-35 printed Apr. 2, 2018.
Catalog from http://www.bd.com/sharps/pdf/Disposal_Solutions_Product_Catalog.pdf accessed Feb. 4, 2015.
MSDS of Absorb-O-Gel from http://www.medline.com/media/catalog/Docs/MSDS/mph17cd410%20-%20div.%2010.pdf dated 2005, accessed Feb. 4, 2015.

* cited by examiner

SYSTEM AND METHOD FOR PACKAGING AN ABSORBENT FOR SOLIDIFICATION OF LIQUID MEDICAL WASTE

This application is a continuation of application Ser. No. 16/122,046 filed Sep. 5, 2018, which is a continuation of application Ser. No. 13/966,685 filed Aug. 14, 2013, which claims the benefit of Provisional Application Ser. No. 61/682,960 filed Aug. 14, 2012.

FIELD OF TECHNOLOGY

Conventional medical waste solidifiers are contained in bottles or packets and are used successfully in many hospitals and surgical centers throughout the country. However, there is inconvenience in shipping, storage and handling solidifier, as well as risk associated with post procedure handling of the suction canister waste, leading to a need for a safer, quicker, and more efficient shipping, delivery and packaging method.

BACKGROUND

Liquid medical waste, typically from a surgical procedure, is flowed into medical waste containers. The liquid medical waste is deposited under the influence of a suction, which directs the liquid through a conduit. The waste is usually an aqueous fluid mixture of saline, blood, urine, and/or other bodily fluids. Regulations require that the liquid be converted to a solidified form prior to transport in order to minimize the possibility of hazardous waste being spilled.

Solidifiers in various forms have been used in attempts to meet regulations, solidify hazardous wastes and to prevent spillage upon disposal of the waste filled containers. Previously, absorbents have been provided to hospital and surgical center personnel as a solidifier to be measured and dispensed into the waste container and/or in packaged pre-filled solidifier packets and bottles to be added to the container with instructions to add the solidifier after all of the expected waste fluid has entered the container.

Solidifiers have attempted to reach firm solidification, where no fluids will spill when the container is turned on its side; however, a problem with "gel block" has persisted. Development of "gel block" prohibits firm solidification. "Gel block" occurs when the inflowing aqueous mixture becomes solidified and sections off portions of the fluid so that it cannot reach available solidifier. When gel block occurs, the aqueous fluid does not firmly and completely solidify and spillage during transport is problematic.

Previously, the problem of "gel block" has been addressed in a variety of ways. Various solidifiers with different densities have been combined so that the solidifier will migrate to specific levels or zones of the fluid. However, weighted solidifiers take some time to reach their separated levels, and the use of swifter solidifiers with this system still presents problems with "gel block." Additionally, the speed with which the fluid is introduced and the timing of the release of weighted solidifier is extremely important if the weighted solidifier is to inhibit "gel block."

Superabsorbants are known in the art as water-swellable, water-insoluble, organic or inorganic material capable of absorbing at least about 100 times its weight and up to about 300 times its weight in an aqueous solution. Superabsorbent polymers are cross-linked, neutralized polymers which are capable of absorbing large amounts of aqueous liquids and body fluids, such as urine or blood, with swelling and the formation of hydrogels, and of retaining them under a certain pressure in accordance with the general definition of superabsorbent. The main use for internally cross-linked superabsorbent polymers has been in sanitary articles.

A trend in sanitary articles, for comfort and sanitation reasons, has been to make them smaller and reduce their size. To do this, much of the fluff fiber in these articles has been removed and more superabsorbent polymer has been added. With less structure provided, more superabsorbent polymer is needed in sanitary articles along with a higher gel strength. However, increasing gel strength in cross-linked superabsorbent polymers often results in less polymer swellability, permeability and retention capacity. U.S. Pat. No. 7,291,674 to Kang, herein incorporated by reference in its entirety, addresses surface cross-linking, superabsorbent polymers in order to retain liquid retention, permeability, and gel bed strength when superabsorbent polymer is increased in percent by weight based on the absorbent structure.

Additionally, it is known in some fields to add non-polymeric particles to internally cross-linked superabsorbent polymers in order to increase the swellability of the superabsorbent polymers. In fiber optic applications, the cables are coated with a mixture of superabsorbent polymer and non-polymeric silica particles. If the cable covering is breached and fluid seeps inside, the mixture leads to "gel block" and acts as a gelling agent where the suberabsorbent polymers have enhanced swellability so that they water block. In such an application, gel block is desired and the particle mixture is designed to achieve gel block as a desired end result.

While advancements in the solidifiers that absorb the hazardous wastes have increased absorbency and decreased the chance of spillage, the challenges associated with the most effective and efficient delivery and storage of the absorbents remains. When solidifier is provided in bottles, the bottles are bulky to ship and require a large amount of storage space on site. Bottled solidifier is typically measured and dispensed into the container after the introduction of liquid wastes, so that personnel are exposed to extensive handling of the container, solidifier and container covers. In addition, some solidifiers are believed to have carcinogenic properties, so exposure of the solidifier to the hospital personnel may be hazardous. After being emptied, the solidifier bottles add to the large amounts of waste that must be disposed of or recycled in hospital or medical facilities.

Even when packets prefilled with solidifier are used, they still take up excess storage space. Typically, prefilled packets must be placed into the container by personnel in sufficient solidifier quantities to accomplish complete solidification. If solidifier packets are added prior to the introduction of waste fluid, the amount of solidifier to completely solidify the volume of fluids able to be held within the waste container is used. Many times, the amount of waste fluids gathered during a procedure may be significantly less than that amount capable of being accumulated within the container. Thus, more solidifier is used than is necessary to completely solidify the contents of the container.

In some instances, medical personnel wish to quantify the amount of waste fluid gathered in a waste container during a procedure. Use of prefilled packets prior to measuring the waste contents may displace the fluid and skew the resulting fluid measurement. As such, there remains a need in the art for providing an improved delivery system for solidification of medical container wastes. It is to some of these or additional problems that the present disclosure is directed.

SUMMARY OF THE INVENTION

The inventions of the present disclosure fulfill one or more of these needs in the art by providing an improved storage and delivery system for an absorbent for solidification of liquid wastes. In one embodiment, the system includes a plurality of containers that are nested to form at least one packet safe space (PSS) and a packet containing an amount of solidifier that is contained within the PSS.

The plurality of containers each has a bottom. The containers are nestable one within another to form the PSS between the bottoms of the containers when they are nested one within another. The PSS may include a height and a width.

Each packet may include an amount of solidifier capable of solidifying the volume of aqueous liquid accommodated by the containers. The packets may be completely dissolvable or may be partially dissolvable in an aqueous liquid. The packets are adapted to release at least a portion of the solidifier into the aqueous liquid. In one embodiment the packets may have a dry burst threshold and be adapted to fit within the height and width of the PSS so that the dry burst threshold of the packet is not exceeded. The packet may be configured to be pre-loaded into the container prior to the addition of liquid medical waste.

The system may further include an adhesive for securing the packet within the packet safe spaces.

The solidifier may include a plurality of cross-linked superabsorbent particles. The particles may be internally and/or surface cross-linked superabsorbent polymer particles. The solidifier may further include a plurality of second particles with diameters substantially smaller than the diameters of the polymer particles. The second particles, by way of example, may be inorganic non-soluble particles. The polymer particles and the second particles may be electrostatically attracted to one another. The solidifier may further include a sanitizer.

In one embodiment, the bottoms of the containers may include a projection that extends upward into a medial area of the container. The packet may be adapted to fit within the packet safe space area that surrounds the projection. In one embodiment, the packet may have sides that are substantially longer than its ends. In one example, a packet side may be at least twice the length of an end. Applicant realized that such configuration not only allows the packet to fit efficiently around a projection found in the bottom of many waste containers, but also the packet may be adapted to fit through an opening in a container lid already placed securely on the waste container. This adaption allows the user the option of choosing to leave packets pre-loaded or add the packets during or after a procedure where waste fluids are introduced. In this embodiment, users may add an amount of solidifier in a packet to the container and then later add additional packets containing solidifier to the container without removing the container lid if more solidifier is needed. Therefore, the invention may also be considered an improved packaging system and method for solidification of liquid wastes.

In another embodiment, the containers may include outward bulging bosses on their tops. The bosses may be configured so that as a second container is received by a first container, the boss of the second container rests on the top of the first container and prevents the collapse of the second container's bottom to the first container bottom, resulting in a packet safe space between the bottoms.

In an alternative embodiment, the first and second container may have tapered side walls so that the second container is received in the first container and the tapers prevent the second container's bottom from downwardly collapsing excessively into the PSS.

Alternatively, the first and second containers may have standoffs on inside faces of their side walls and above their bottoms. As the second container is received into the first container, the second container may rest on the stand-offs of the first container so as to prevent collapse of the second container's bottom forming the PSS.

The invention may also be considered a method for delivery and storage of a solidifier for solidification of liquid medical waste. The method includes packaging an amount of solidifier suitable to solidify a volume of aqueous liquid into an at least partially soluble packet, placing the packet into a first container having a bottom, nesting a second container into a first container having a bottom, thereby creating a PSS between the bottoms of the containers and housing the packet in the PSS for delivery and storage.

BRIEF DESCRIPTION OF THE DRAWINGS

The invention will be better understood by a reading of the Detailed Description of the Examples of the Invention along with a review of the drawings, in which.

DETAILED DESCRIPTION OF EXAMPLES OF THE INVENTION

Figure 1:
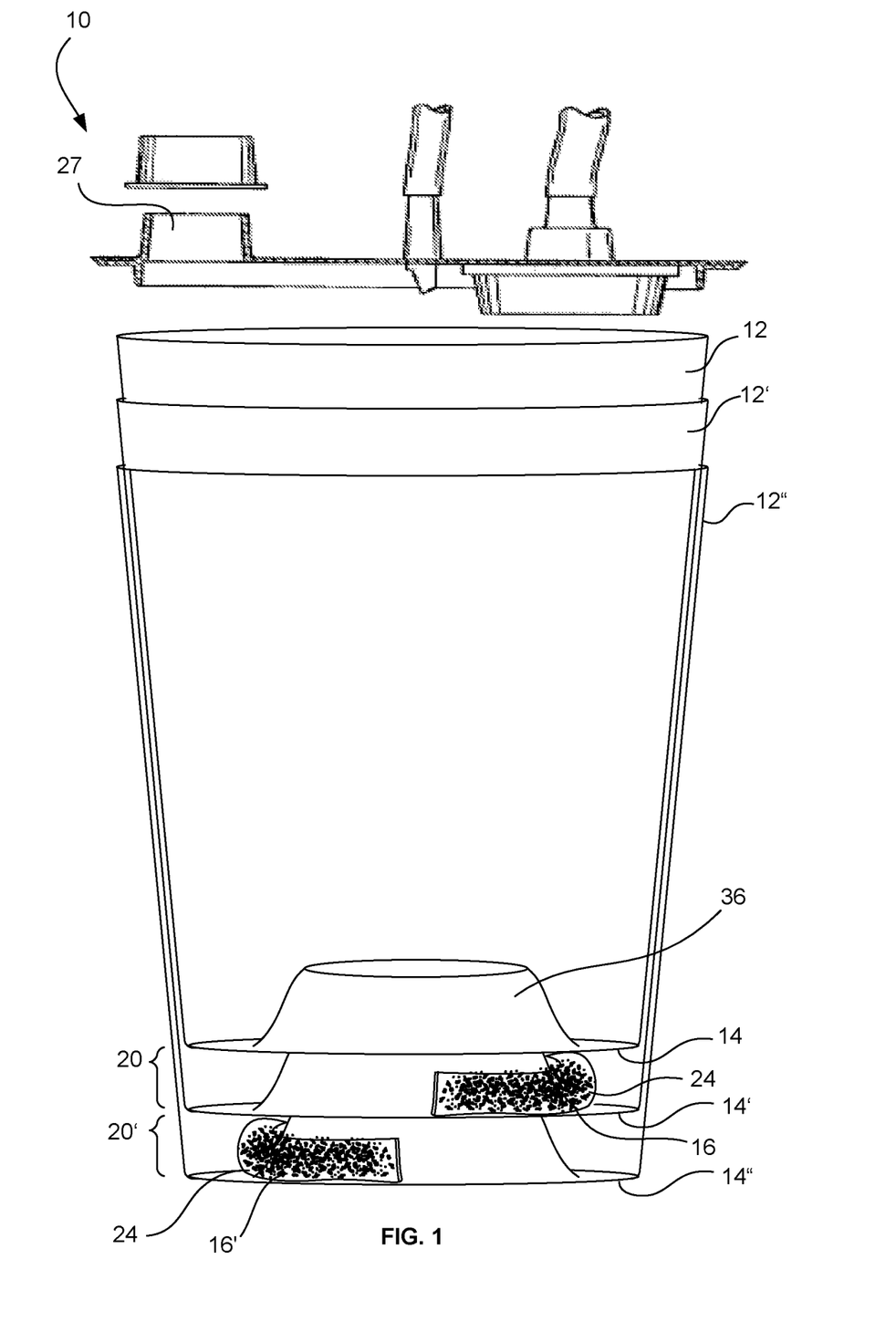
FIG. 1 is a perspective view of one embodiment of a system for delivery and storage of an absorbent for solidification of liquid medical waste.

Referring now to the drawings in general, the illustrations are for the purpose of describing a preferred example of the invention and are not intended to limit the invention thereto. In FIG. 1, the system, generally designated 10, includes a plurality of containers 12, 12', 12" that are nested to form interstitial packet safe spaces (PSS) 20, 20'. The system 10 further includes packets 16, 16' each containing an amount of solidifier 22 and housed within one of the PSS 20, 20'. The container 12, is for example, a medical waste collection container. Such containers are conventional and will not be discussed in detail. Examples of one typical container can be seen in U.S. Pat. No. 6,797,857 to Tanhehco. The plurality of containers 12, 12', 12" each has a bottom 14, 14', 14". The containers are nestable one within another to form the PSS 20, 20' between the bottoms of the containers when they are nested one within another.

A PSS 20 typically contains a packet 16. The packet 16 includes an amount of solidifier 24 capable of solidifying the volume of aqueous liquid to be held in a container 12. The packet 16 may be completely dissolvable or may be partially dissolvable in an aqueous liquid. The packet 16 is adapted to release at least a portion of the solidifier 24 into the aqueous liquid.

In one embodiment, the packet may be made of dissolvable polyvinyl alcohol; however, the packet may be made of any suitable water soluble film. The dissolvable portion of the packet should have disintegration time and temperature suitable to the fluids in which it will be exposed. Another consideration is compatibility of the packet with its contents. The packet should provide for prolonged storage capacity without resulting in insolubility, rigidity or changes in the packet or its contents. Examples of such compatible films are dissolvable films that can be acquired from MonoSol, LLC, such as their models M7031, M7061, M8534, and M8900 (PXP6829) of water soluble film. Optionally, water soluble paper may be used. The dissolvability of packet 16 allows the packet to be placed into a container 12 prior to introducing fluids into the container. The dissolvable packets 16 provide a cost effective way to minimize risk of exposure for medical workers. The packets 16 allow hospital staff to avoid handling of the solidifier 24 after fluids have been introduced. Conventional powder solidifiers or loose absorbents are usually added after fluid is introduced into a container and require handling of the solidifier and/or risk exposure to the waste fluids by the medical personnel.

Figure 2:
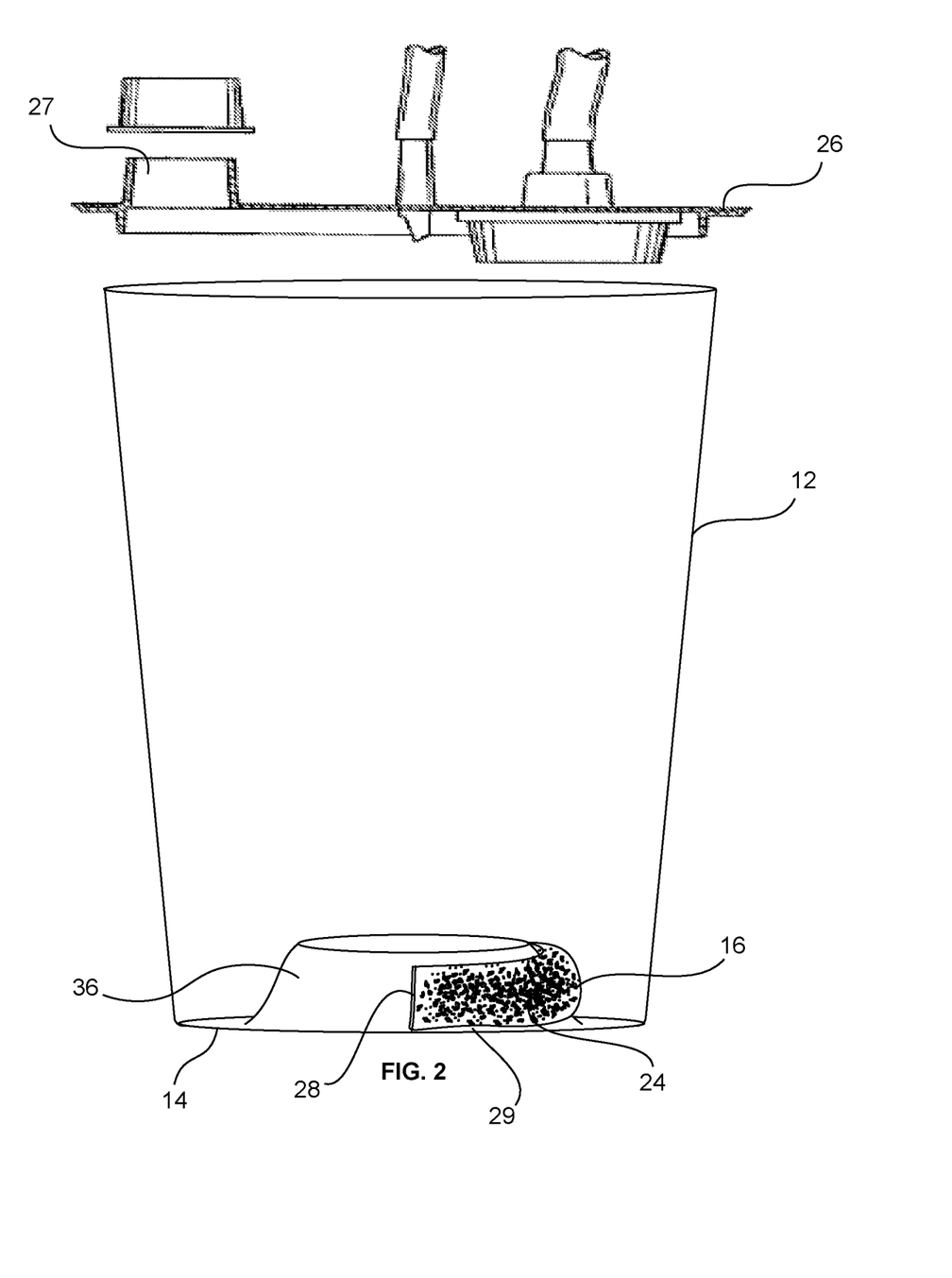
FIG. 2 is a perspective view of a container housing a packet having a solidifier for absorbing aqueous liquid to be solidified.
Figure 3:
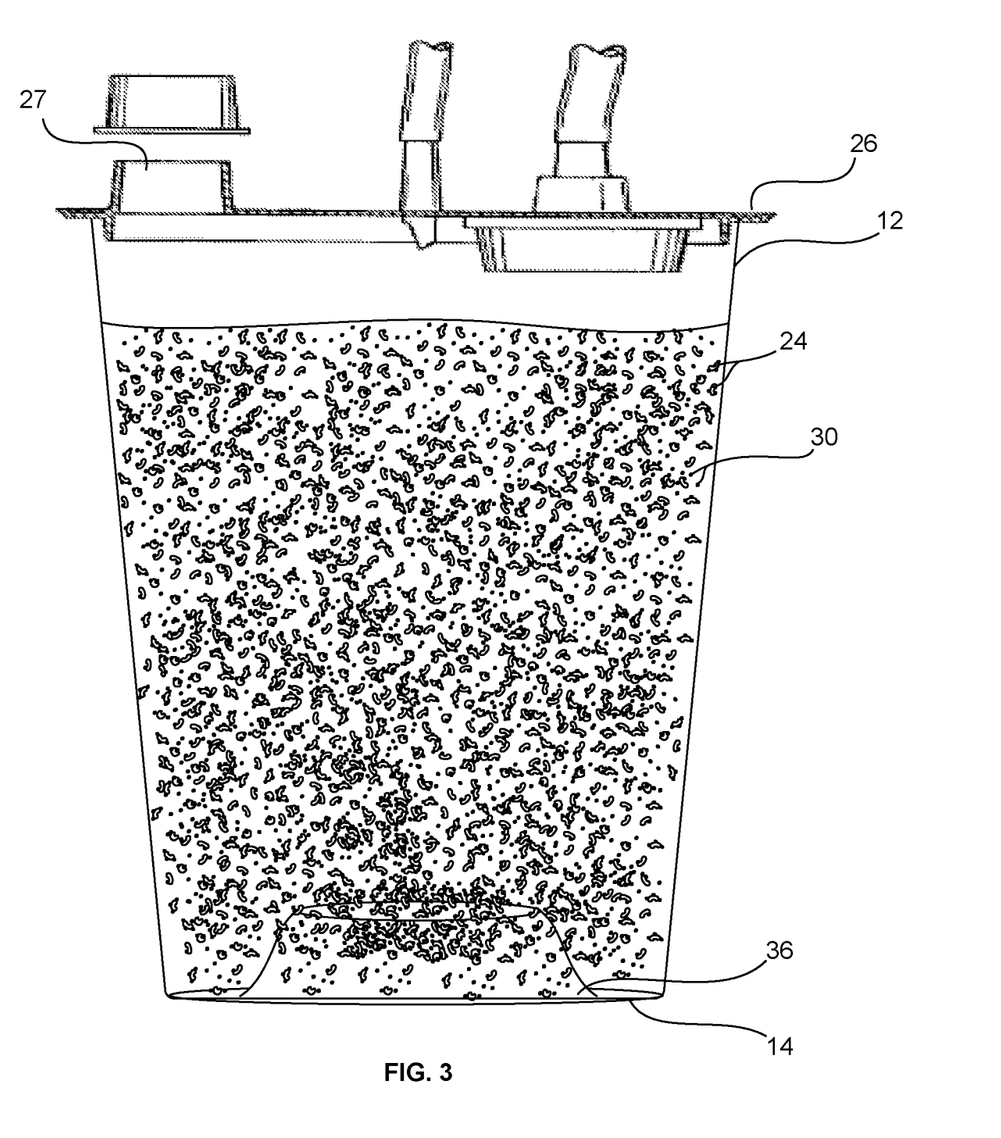
FIG. 3 is an illustration of the solidifier being released from the packet and into the aqueous liquid to be solidified.

In operation, as may be seen in FIGS. 1-3, packet 16 containing solidifier 24 is loaded into a container 12' in preparation for shipping. Container 12 may be nested into the second container 12' forming a PSS 20. Another packet 16' is loaded into a container 12" and then container 12' nested into container 12" forming a stack of containers with packets, each housed inside an individual PSS for shipping and storing. The stacks of containers may include any variable number of containers and packets; however, typically containers may be stacked in groups of ten to twenty for optimal shipping and storage conditions. This arrangement alleviates multiple shipping costs and packaging by allowing the containers and the packets to be packed and shipped together. Inventory requirements are also reduced as both the packets and containers may be inventoried and stored together.

Additionally, the PSS houses and protects the packets during shipping and storage and eliminates the need for separate storage spaces for the containers 12 and the packets 16 filled with solidifier 24. However, packing and shipping the containers and packets together is challenging because the packets must be protected during shipping and storage. The size of the PSS 20 is a limiting factor, as is the amount of the solidifier that is needed to solidify the volume of liquid that may fit within the container. Therefore, an adequate amount of solidifier 24 has to be packaged in a manner that it will be accommodated in the PSS 20 so that the dry burst threshold of the packet 16 is not exceeded. A PSS that is too small, an inadequate amount of solidifier or a packet that is too large or cumbersome are all variables that may render the solidifier ultimately ineffective in use for the solidification of liquid wastes. As seen in FIGS. 1-2, in one example applicant overcomes these limiting variables, as in a container with a raised projection 36 in a bottom of the container, by way of a packet 16 with a flexibility sufficient to be molded and/or bent around the projection 36 so that the packet is contained between the projection 36 and a side of the container. Because the surface crosslinked super absorbent polymer maintains a permeability in a gel bed in an aqueous solution surround, instead of forming a gel block and sectioning off portions of unsolidified liquid, the packet may be prepackaged in the container 12, for shipment without a concern of bursting and prior to the addition of fluid wastes into the container. The packet 12 is able to avoid gel block in aqueous environments without the constraints of packet positioning within the container 12 and/or without requiring the addition of variable kinds of solidifier in the packet, such as the approach taken by Tanhehco of adding variable density solidifier to work around the gel block issue that is created by the use of the Tanhehco solidifier.

Figure 4:
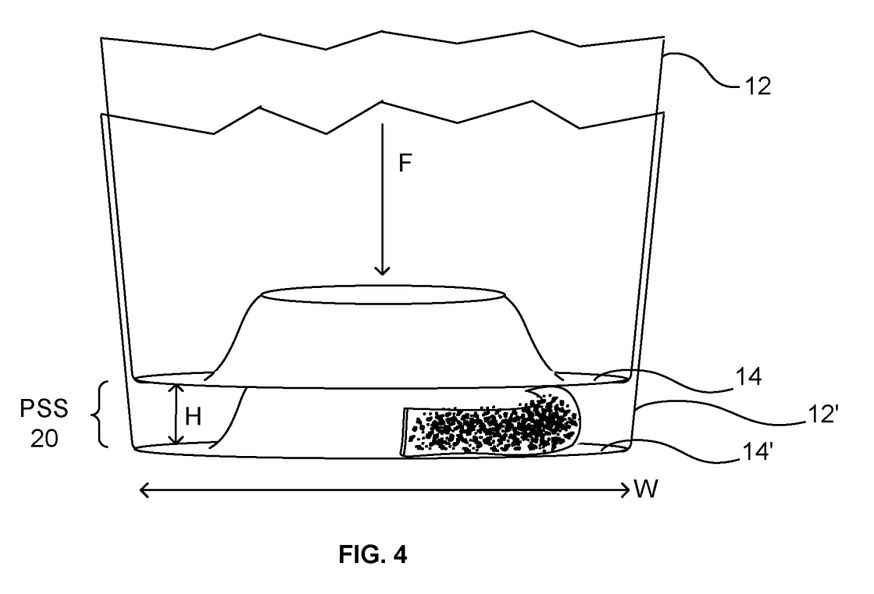
FIG. 4 is a perspective view of a packet housed within a container in a Packet Safe Space.

As seen in FIG. 4, the PSS may include a height (H) and a width (W). In one embodiment, the packet 16 may have a dry burst threshold and be adapted to fit within the H and W of the PSS so that the dry burst threshold of the packet is not exceeded by the pressure of one container against the other. However, it is desirable for the PSS to be minimized in order to stack and store the containers 12 as compactly as possible. The PSS should be of a sufficient H and W to accommodate a packet filled with an amount of solidifier able to solidify the volume of fluid accommodated by the particular container. The dry burst threshold is exceeded when the downward force F of the bottom 14 causes the packet within the PSS to rupture and/or burst. A slight interstitial space between the packet and the bottom 14 assists in preventing exceeding the dry burst threshold. Typically, the H of the PSS may range from between 1 to 4 centimeters and may vary, depending on the volume of the container 12. Typically, the W of the PSS may range from between 9 to 12 centimeters and may vary depending on the volume of the container 12. However, it is to be understood that a PSS outside of the specified H and W may be necessary to accommodate an amount of solidifier, a container or a packing/storage restraint and is considered within the scope of this invention.

In order to maintain packet integrity during packing and shipping, the adequate dosing amount of solidifier, the volume of the containers and the size of the PSS are useful criteria in designing packets with appropriate dimensions. The known dissolvable packets were traditionally rectangular in shape and were difficult to manipulate to accommodate the necessary solidifier while also fitting within the PSS. The rectangular shaped packet has been documented in the art to be desirable and to assist in the positioning of a packet of solidifier as it sinks to the bottom of a vessel when it is placed into the vessel already containing fluid to be absorbed.

In one embodiment, packets 16 are designed to accommodate the desired amount of solidifier and to have a squared or rounded cross-sectional shape as opposed to the traditional rectangular shape. Applicant discovered that this shaping allows the packet to fit within the container and to house the desirable solidifier and to avoid some of the challenges as discussed herein with the more traditional rectangular packet configuration. Since Applicant is able to add solidifier prior to the addition of fluid, the disadvantages of non-rectangular packet shaping is overcome in applicant's applicant in this example, and the benefits of the proposed rectangular packing are not required to deal with gel block. The packet may take on other additional shapes which are considered within the scope of this invention.

Once the system 10 has been prepackaged, shipped and stored, by way of example, in a hospital facility, one of the containers in the stack may be removed when solidification of liquid wastes is needed. As seen in FIG. 2, the container may already be preloaded with a packet 16 containing the amount of solidifier 24 suitable for solidification of the amount of liquid able to be accommodated by the volume of the particular container 12. A container lid 26 may be placed onto the container 12 and the container is then prepared to accept medical liquids to be solidified.

The container 12, already containing the packet 16 with solidifier 24, may be sealed and placed under suction by one of the hoses connected to the lid 26 seen in FIGS. 1-3 prior to introduction of the medical waste. As medical waste begins to fill container 12 from the other hose shown in the figures, the packet at least partially dissolves in the fluid, releasing the solidifier into the fluid. As seen in FIG. 3, the solidifier 24 disperses into the aqueous liquid and solidifies the contents of the container 12 for disposal. To meet the standards for proper disposal, the liquid contents must reach "complete solidification" where no fluid pours out if the container is turned on its side. The preloading of the packets 16 into containers 12 for shipping and storage means the container is preloaded with solidifier for use. This allows the container to be sealed prior to, during and after a procedure and personnel never need be exposed to the liquid waste, even in solidified form. At the end of the medical procedure, the liquid waste contents are firmly solidified in a gel and the canister can be taken away for proper staging and ultimate disposal. Post procedure cleanup is streamlined, sanitary and time saving. Unlike prior art configurations that require the addition of solidifier after the medical procedure has generated the liquid to be collected, with applicant's pre-loaded solidifer, solidification can start much earlier and therefore be completed much earlier.

Issues with gel block during solidification, where the inflowing aqueous mixture gels in sections and segments off areas of the fluid so that it cannot be reached by available solidifier, is another variable that should be taken into account when selecting the proper solidifier for inclusion in the packet. When gel block occurs, the aqueous fluid does not firmly and completely solidify, and spillage during transport is problematic and may not properly meet code solidification requirements.

Superabsorbent polymer solidifiers are known to rapidly solidify fluids. However, some superabsorbent polymers solidify so quickly that they may actually cause gel block when fluids are introduced over a period of time. A superabsorbent polymer that solidifies quickly but does not cause gel block is preferable. A suitable superabsorbent polymer may be chosen from a variety of polymer sources, including at least one of natural polymers, biodegradable polymers, synthetic polymers and modified natural polymers, etc. The term cross-linked used in reference to superabsorbent polymers includes any modification for effectively rendering normally water-soluble materials substantially water-insoluble but swellable. Such a crosslinking modification can include, for example, physical entanglement, crystalline domains, covalent bonds, ionic complexes and associations, hydrophilic associations such as hydrogen bonding, hydrophobic associations or Van der Waals forces. Superabsorbent polymers have one or both of internal crosslinking and surface crosslinking. Surface crosslinking includes any process that increases the crosslink density of the polymer matrix in the vicinity of the superabsorbent particle surface with respect to the crosslinking density of the particle interior.

In one embodiment, the solidifier 24 may include a plurality of cross-linked superabsorbent particles. The particles may be internally and/or surface cross-linked superabsorbent polymer particles such as the superabsorbent polymers discussed in U.S. Pat. No. 7,291,674 to Kang, the entire disclosure being hereby incorporated by reference. Applicant realized that while Kang deals with dry, absorbent under load conditions, modifications could be made by Applicant to adapt such surface crosslinked superabsorbent polymers for usage in an aqueous environment. In another example, surface cross-linked superabsorbent polymers as available from Stockhausen, Inc. of Greensboro, N.C. or from Zappa Tec, LLC of McLeansville, N.C., as AP95, may be suitable as a superabsorbent polymer for Applicant's invention.

The amount of solidifier to be contained within a packet often varies depending on the volume (V) of the container to be solidified. Typically, the container volume (V) varies from about 500 cc to about 16000 cc. By way of example, an amount of solidifier (S) may include between 20 and 40 grams of superabsorbent polymer particles per 1000 cc of fluid to be solidified. Typically, for example, about 15-25 grams of superabsorbent polymer may be included in a 500 cc container packet, 30-40 grams in a 1000 cc container packet, 43-53 grams in a 1500 cc container packet and 85-95 grams in a 3000 cc container packet. Typically, an amount of solidifier (S) may be present in a packet in the range of about 1 gram to about 500 grams.

The solidifier 24, as seen in FIG. 3, may further include a plurality of second particles 30 with diameters substantially smaller than the diameters of the polymer particles. The second particles 30, by way of example, may be inorganic non-soluble particles. In one embodiment, the second particles 30 may be hydrophilic fumed silica as is offered by Evonik Industries as AEROSIL® 200. While not the preferred embodiment, other additives such as silicates, kaolin, zeolites and bentonite may be used. The polymer particles and the second particles may be electrostatically attracted to one another with the second particles substantially interspaced around the superabsorbent particles. When surface and interior cross-linked superabsorbent polymers begin to absorb the aqueous fluid and swell, the second particles assist in maintaining a space between the polymer surfaces. This space may serve as liquid flow channels for the fluid, essentially preventing gel block. The specifics of the second particles and the liquid flow channels are disclosed in Applicant's application Ser. No. 12/752,688, which is herein incorporated by reference in its entirety.

The solidifier 24 may further include a sanitizer. Including a sanitizer in the solidifier with the superabsorbent polymer and the second particles assists in further neutralizing the contaminants in the liquid medical waste, reducing handling risk. However, sanitizer may itself be caustic to handlers, therefore, the need to minimize personnel exposure to the solidifier and solidified liquid remains equally important. Any suitable granular sanitizer may be used, one such suitable sanitizer, by way of example, may be sodium dichloro-s-triazinetrione dihydrate known as ACL® 56 Chlorinating Composition and available from OxyChem® of Texas.

Dissolvable films for packets should maintain proper functionality even with the addition of the sanitizer. Some sanitizers may have properties that cause the breakdown of certain dissolvable films. Similar considerations as discussed above for the packets would apply here as well, with the additional consideration of the impact of a sanitizer on the packet film. Examples of such packets considered compatible with the sanitizer are, by way of example, the dissolvable films that can be acquired from MonoSol, LLC, known as models M7031 and M8900 (PXP6829) of water soluble film.

The system may further include an adhesive for securing the packet 16 within the PSS 20. Any such adhesive is feasible as long as it does not adversely interfere with the stability of the packet 16. In one embodiment, a hot melt adhesive may be used to secure the packet 16 within the PSS 20. One example of a suitable hot melt adhesive is PS-2200 as available from Gluefast of Neptune, N.J.

As seen in FIG. 1, the bottoms 14 of the containers 12 may include a projection 36 that extends into the medial area of the container above the bottom. The packet 16 may be adapted to fit within the area of the PSS that surrounds the projection.

Figure 5:
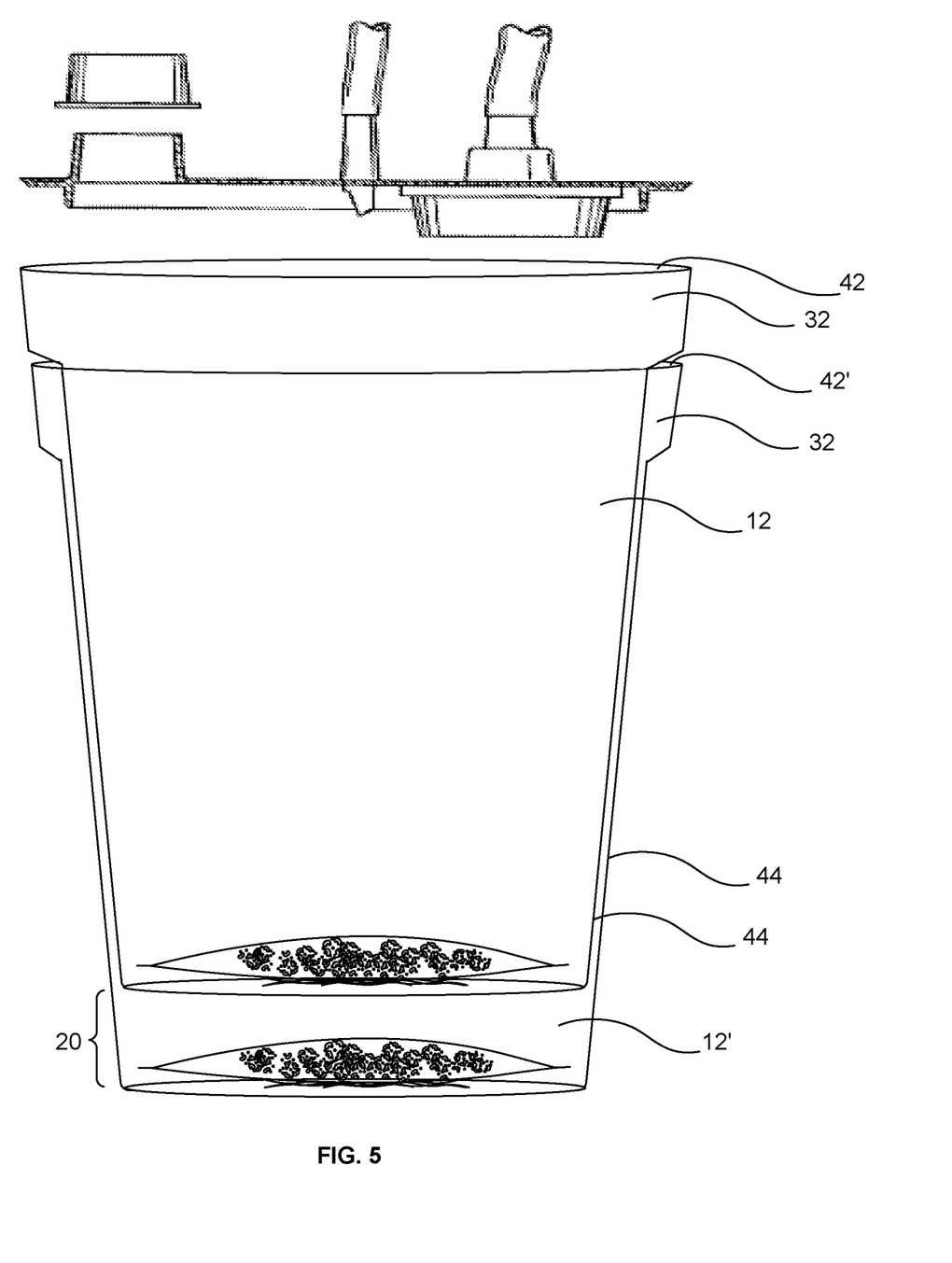
FIG. 5 is an alternative embodiment of a system for delivery and storage of an absorbent for solidification of liquid medical waste.

In another embodiment seen in FIG. 5, the first and second container 12, 12' may include outward bulging bosses 32, 32' located near their respective tops 42, 42'. The bosses may be adapted so that as the first container 12 is received by the second container 12', the boss 32 of the first container rests on the top of the second container and prevents the collapse of the first container's bottom into the PSS 20. The boss 32 may be wider or smaller in width to provide for a PSS having a greater or lesser H. In one embodiment, a packet 12 may be a circular packet able to fit flush into the container bottom, and in some examples, while spanning the bottom surface substantially across the diameter of a container bottom. In this example, the circular packet takes up a minimal amount of space while still maintaining a maximum amount of surface area for dissolving the packet, releasing the superabsorbent polymer, resulting in a faster solidification of the liquids to be solidified. Further, with some examples of inventions of the present disclosure, gel block is avoided in situations where the packet is pre-packaged in the container prior to the addition of fluids and fluids are accumulated/added to the container over a period of time, for example, fluids being accumulated over the course of a surgery, as opposed to placing a packet in a container once all of the fluids to be solidified have already been collected in the container.

In an alternative embodiment, the first 12 and second container 12' may have tapered side walls 44, 44' so that the first container 12 is received in the second container 12' and the tapers prevent the first container's bottom from collapsing into the PSS 20. The taper of the side walls may be increased or decreased to provide for a greater or smaller PSS H.

Figure 6:
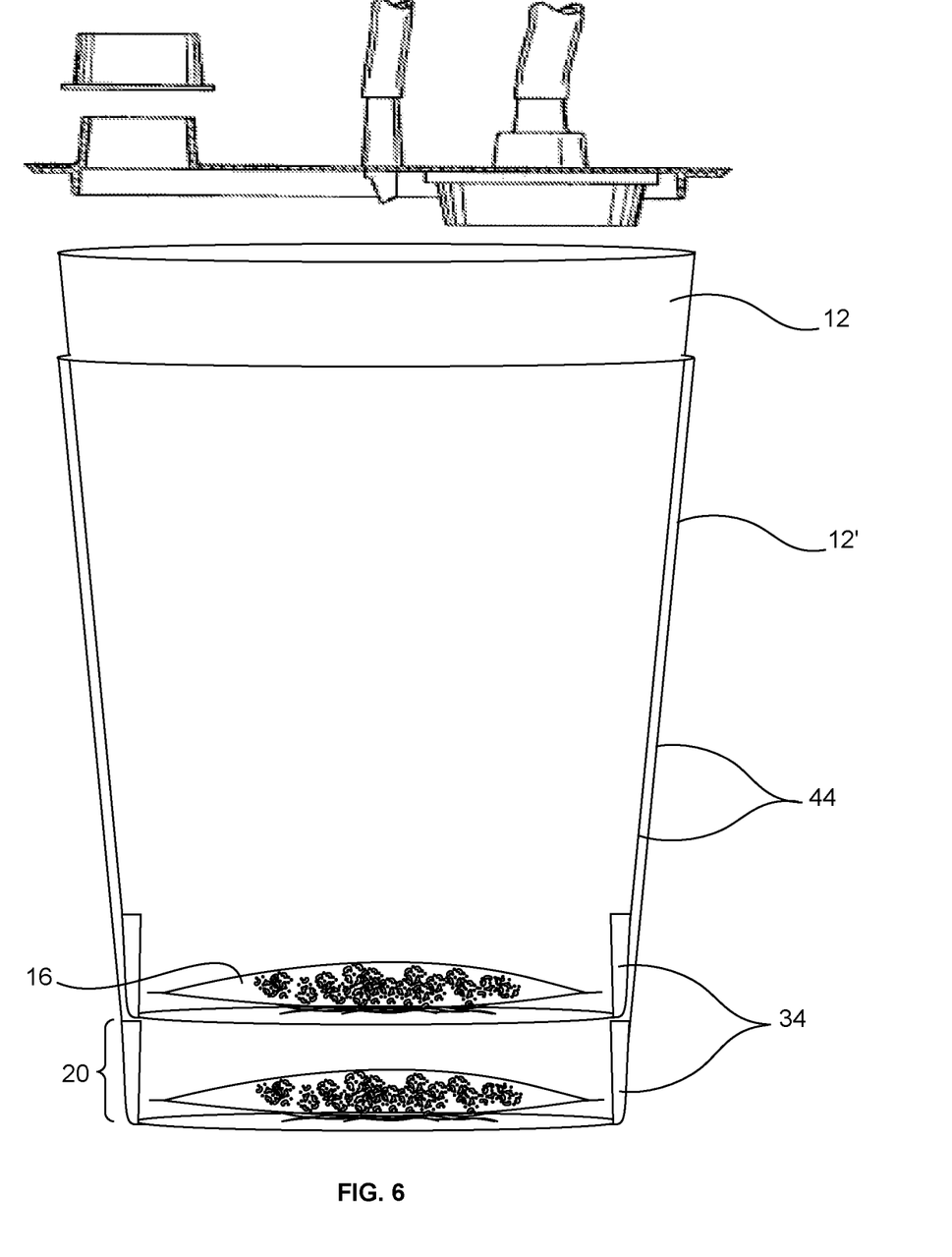
FIG. 6 is an alternative embodiment of a system for delivery and storage of an absorbent for solidification of liquid medical waste.

Alternatively, as seen in FIG. 6, the first and second containers 12, 12' may have standoffs 34 on inside faces of their side walls 44 and above their bottoms 14. The standoffs may be, by way of example, small, flat, fin-like inward projections from the sidewalls of the containers. As the first container 12 is received into the second container 12', the first container may rest on the one or more stand-offs 34 of the second container 12' so as to prevent collapse of the first container's bottom into the PSS 20. Such stand-offs are known for some nestable plastic containers to ease their separation from one another.

The invention may also be considered a method for delivery and storage of a solidifier 24 for solidification of liquid medical waste. The method includes packaging an amount of solidifier suitable to solidify a container volume of aqueous liquid into an at least partially soluble packet 16, placing the packet into a first container 12 having a bottom 14, interfacing the first container 12 with a second container 12' having a bottom 14', creating a PSS 20 between the bottoms of the containers and housing the packet 16 in the PSS for delivery and storage.

In one embodiment, housing the packet 16 in the PSS 20 pre-loads the solidifier into the second container 12' while the containers are in inventory and prior to the addition of aqueous liquids to the second container.

The method may also include subsequently introducing liquid medical waste into the second container 12' and thereby dissolving at least a portion of the packet 16 in the second container 12' in the liquid medical waste; releasing solidifier from the dissolved portion of the packet; and solidifying the liquid medical waste inside the second container.

Figure 7:
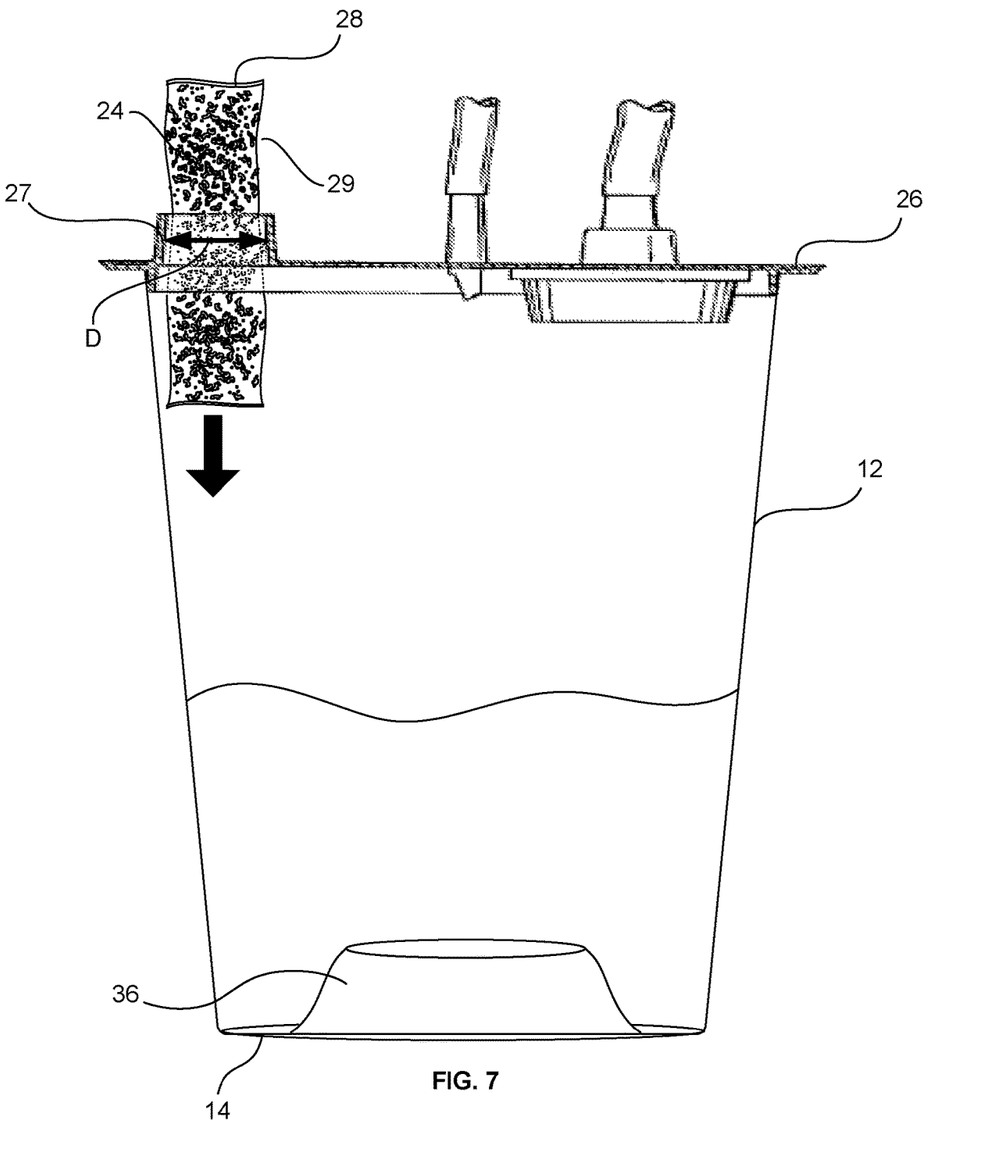
FIG. 7 is a perspective view of one embodiment of an improved system for packaging an absorbent for solidification of liquid medical waste.

Further disclosed, as seen in FIGS. 1, 2 and 7, the packet 16 may be adapted to fit within the volume of the PSS. Typically, the packet is generally cylindrical and elongated with cylinder sides that are substantially longer than its diameter. In one example, a packet side 28 may be at least twice the length of a packet end 29. The packet may take on other shapes that are still within the scope of this invention.

In another example, a cross-sectional size (S) of a packet is less than the diameter (D) of the opening/port 27 in the lid 26, so that the packet 16 is adapted to fit through the opening. Typically, opening/port 27 measures approximately 1 inch in diameter and Applicant had to overcome the limited access size of the port while still configuring a packet that contains enough solidifier to firmly solidify the waste fluids but still fits within the PSS. Opening/ports may take on other diameters and packets may be designed with suitable cross-sections to allow insertion in such openings.

This configuration not only allows the packet to fit efficiently around a projection found in the bottom of many waste containers, but also the packet may be adapted to fit through an opening 27 in a container lid already placed securely on the waste container. This adaptation allows the user the option of choosing to leave packets 16 pre-loaded or add the packets during or after a procedure when waste fluids have already been introduced. Also in this embodiment of the packet, users may add an amount of solidifier in a packet to the container and then later add additional packets containing solidifier to the container without removing the container lid, if more solidifier is needed. Some containers may have lids 26 that are sealed and not removable from the container 12. Applicant's packet, adapted to fit through an opening or port 27 in the lid 26, provides options not previously available to medical personnel to add variable amounts of solidifier at variable times to such containers throughout a procedure. Therefore, the invention may also be considered an improved packaging and delivery system and method for solidification of liquid wastes.

Certain modifications and improvements will occur to those skilled in the art upon reading the foregoing description. It should be understood that all such modifications and improvements have been omitted for the sake of conciseness and readability, but are properly within the scope of the following claims. For example, although the primary intended use is for liquid medical waste, other aqueous liquids could be solidified. Also, although the film is preferably all dissolvable, it is within the scope of the invention to make only parts dissolvable.

What is claimed is:

1. A system comprising:
   a plurality of medical waste containers, each container having a bottom and a projection that extends from a bottom inner surface of the container, the containers being configured so that the containers are nestable one within another to form, between each container and a second container within which the container is nested, a packet safe space between the bottom of the container and a bottom inner surface of the second container within which the container is nested;
   within each packet safe space corresponding to each container, a corresponding packet at least partially dissolvable in an aqueous liquid, the packet molded around at least a portion of the projection of the container; and an amount of solidifier, contained within each packet, capable of solidifying a volume of the aqueous liquid accommodated by one of the containers, wherein, when the volume of the aqueous liquid is introduced into the one of the containers, the corresponding packet is configured to release at least a portion of the amount of solidifier into the volume of the aqueous liquid to achieve firm solidification of the introduced volume of the aqueous liquid.

2. The system of claim 1,
wherein a volume of each container is between about 500 cc and about 16,000 cc, and
wherein the amount of solidifier within each packet is between about 1 gram and about 500 grams.

3. The system of claim 1, wherein the solidifier comprises a sanitizer.

4. The system of claim 1 further comprising adhesive securing each packet within the packet safe space containing the packet.

5. The system of claim 1, wherein the solidifier comprises a plurality of particles having a first diameter and a plurality of particles having a second diameter.

6. The system of claim 1, wherein the amount of solidifier within each packet includes between about 15 grams and about 25 grams of a surface crosslinked superabsorbent polymer particle.

7. The system of claim 1, wherein each packet comprises a first side having a first length and a second side having a second length, wherein the first length is at least twice the second length.

8. The system of claim 1, wherein each packet is cylindrical.

9. The system of claim 1, wherein each packet safe space has a height between 1 cm and 4 cm.

10. The system of claim 1, comprising a plurality of lids configured to attach to the plurality of medical waste containers, the lids each having a port,
wherein each packet has a cross-section, and
wherein the cross-section is smaller than a dimension of the port and shaped substantially similar to the port.

11. A method, comprising:
packaging solidifier into each of a plurality of packets, wherein each packet comprises a material that is at least partially soluble in an aqueous liquid, and wherein each packet is at least partially flexible;
at a production facility, assembling a stack of containers, wherein each container comprises a projection that extends from a bottom inner surface of the container, such that, as each container nests in a container below, the container defines a packet safe space between a bottom of the container and a bottom inner surface of the container below; and
during assembly of the stack of containers, inserting, into each packet safe space, a corresponding packet of the plurality of packets, and molding the corresponding packet around at least a portion of the projection of the container having a bottom inner surface defining the packet safe space.

12. The method of claim 11, comprising:
separating a first container from the stack of containers, the first container containing a first packet of the plurality of packets; and
directing liquid medical waste into the first container, such that the first packet at least partially dissolves and solidifier within the first packet solidifies the liquid medical waste.

13. The method of claim 11, wherein a length of each packet of the plurality of packets is less than a circumference of the projections of the containers.

14. The method of claim 11, wherein the projection of each container extends into a medial area of the container.

15. The method of claim 11, comprising, during assembly of the stack of containers, securing each corresponding packet within the corresponding packet safe space by an adhesive.

16. The method of claim 11, wherein the solidifier comprises a plurality of crosslinked superabsorbent polymer particles.

17. The method of claim 16, wherein the plurality of crosslinked superabsorbent polymer particles are internally and surface cross-linked.

18. The method of claim 16, wherein the solidifier comprises a plurality of second particles having diameters smaller than diameters of the plurality of crosslinked superabsorbent polymer particles.

19. The method of claim 18, wherein the plurality of crosslinked superabsorbent polymer particles and the plurality of second particles are electrostatically attracted to one another.

20. The method of claim 11, wherein each packet of the plurality of packets has a circular cross-section.

* * * * *